United States Patent [19]

Ruffa

[11] Patent Number: 5,108,393
[45] Date of Patent: Apr. 28, 1992

[54] NON-INVASIVE BODY-CLAMP

[75] Inventor: Anthony A. Ruffa, Niantic, Conn.

[73] Assignee: The United States of America as represented by the Secretary of the Navy, Washington, D.C.

[21] Appl. No.: 685,064

[22] Filed: Apr. 8, 1991

[51] Int. Cl.⁵ .................................................. A61F 5/04
[52] U.S. Cl. ........................................ 606/56; 606/58; 606/201
[58] Field of Search ................................ 606/54-57, 606/201-203, 152, 153, 58

[56]  References Cited
U.S. PATENT DOCUMENTS

| 3.254.650 | 6/1966 | Collito | 606/153 |
| 4.615.338 | 10/1986 | Llizarov | 606/58 |
| 4.667.672 | 5/1987 | Romanowski | 606/202 |
| 4.691.738 | 9/1987 | McCune | 606/203 |
| 4,973,331 | 11/1990 | Pursley | 606/58 |

Primary Examiner—Robert A. Hafer
Assistant Examiner—David J. Kenealy
Attorney, Agent, or Firm—Michael J. McGowan; Prithvi C. Lall; Michael F. Oglo

[57] ABSTRACT

The present invention discloses a means for providing tension to bones during the healing process that is non-invasive. In the preferred embodiment, the disclosed means for placing bones under tension comprises a first collar and a second collar. Each collar is controllably moved cyclically between a body member embracing condition and a body member releasing condition in such manner that when one collar is in one condition the other is in the other condition. A firm grip is therewith always maintained on the body member while allowing the circulation thereof.

8 Claims, 2 Drawing Sheets

NON-INVASIVE BODY-CLAMP

STATEMENT OF GOVERNMENT INTEREST

The present invention may be manufactured and used by or for the Government of the United States of America for governmental purposes without the payment of any royalties thereon or therefor.

BACKGROUND OF THE INVENTION (1) Field of the Invention

This invention relates to the placing of bones under tension during healing.

(2) Description of the Prior Art

Under certain circumstances, broken bones need tension applied to them during the healing process. Depending on the bone involved, current methods require drilling a hole into the bone to allow a pin to be inserted. Cables are then connected to the pin to facilitate the application of appropriate tension.

This use of pins, however, has serious drawbacks. One of the greatest risks is that of infection, the risk increasing with the time of fixation. Skin and soft tissue necrosis, and bone necrosis at the pin contact point, are also problems. Additionally, chronic osteitis of the bone is a possibility. A non-invasive alternative could substantially eliminate these health risks.

External clamps with cables attached would suffice for the application of tension, but the ensuing restriction of circulation to the flesh in contact with the clamp could result in gangrene, tissue damage and, among other complications, infection. This is because the flesh directly in contact with a static clamp, i.e., the flesh near the surface of the skin, experiences restricted blood flow. It is this surface flesh that can become gangrenous. Such a clamp should of course never be so tight as to completely restrict blood flow to the rest of the limb.

SUMMARY OF THE INVENTION

The principal object of this invention is a non-invasive body clamp to provide tension on a body member to facilitate healing without risking gangrene, tissue damage, infection and other clamp induced complications. In accord therewith, a first movable collar is connected to a second movable collar, the ensemble being attached to a means for generating tension. In further accord therewith, the collars are cyclically moved in such manner that one collar is always in a state that is in embracing relation with the body part under tension while the other collar is in a state that is in circulation allowing relation to the same body part. As the first and second collars cyclically alternate between their respective states, the ensemble always has one collar gripping the body member so that tension remains applied to the body part under tension while permitting the free circulation of the same body part.

In the preferred embodiment, the collars are mechanically actuable cuffs connected by a rigid link, the rigid link serving both as an attachment anchor to the means for generating tension to the body part and as a spacer holding the cuffs in spaced-apart relation about the body part.

BRIEF DESCRIPTION OF THE DRAWINGS

Other features, objects and benefits of the invention can be more clearly understood with reference to the following description thereof, and to the drawings, in which.

DETAILED DESCRIPTION OF THE PREFERRED EMBODIMENTS

Figure 1:
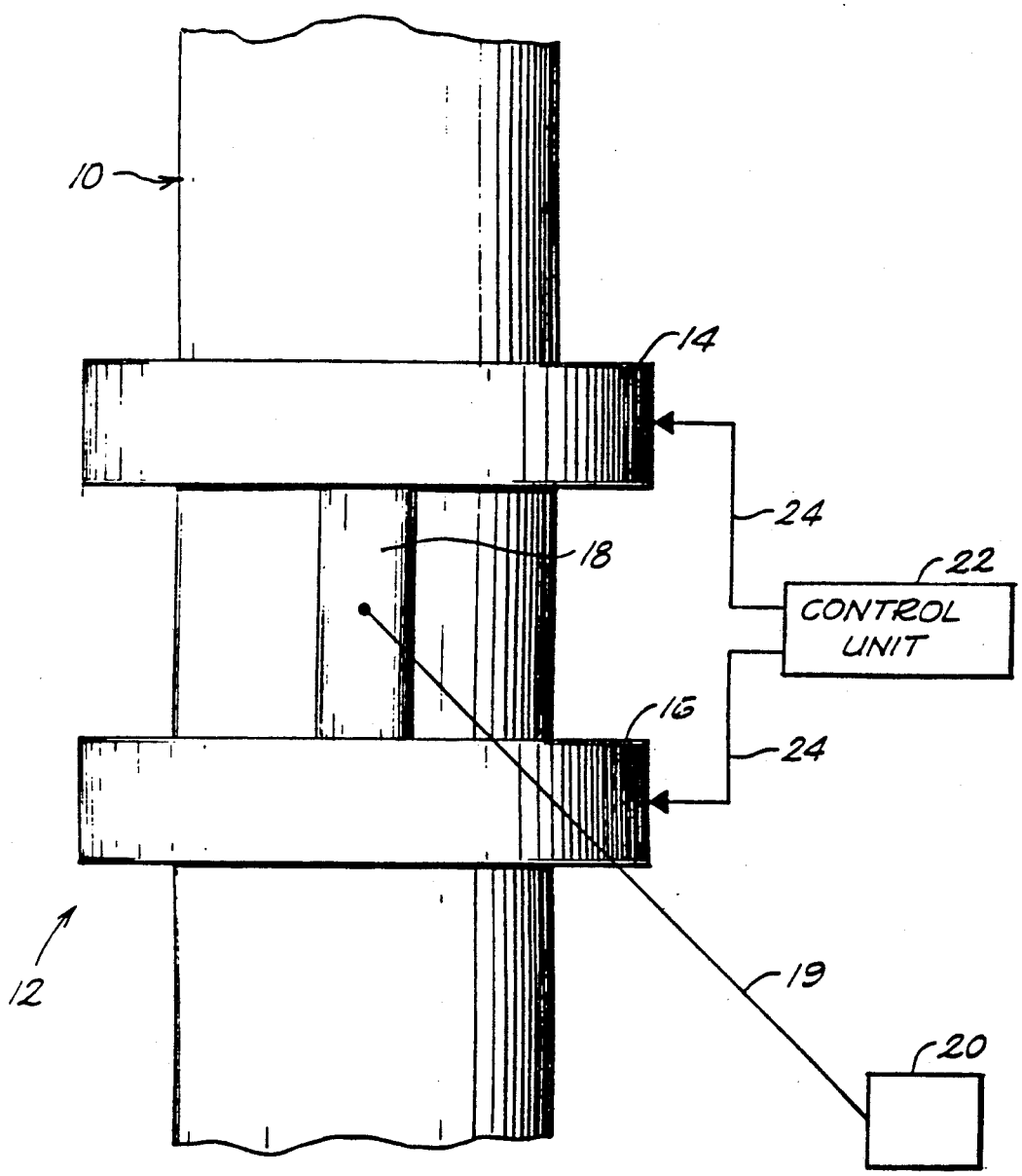
FIG. 1 is a perspective view of a body limb provided with the novel non-invasive body clamp of the invention.

With reference now to FIG. 1, a body limb generally designated schematically at 10 is shown with the clamp assembly generally designated 12 of the invention in position around the limb 10. The limb 10 may be a leg or any other body part to which it is necessary or desirable to apply tension during healing of the same or another body part. The clamp assembly 12 is fabricated in sizes that accommodate differently sized and shaped body parts.

The clamp assembly 12 includes a first clamp 14 connected to a second clamp 16 by link 18. The clamps 14, 16 may be any clamp capable of assuming a first body-part-embracing condition adapted to grip the body limb 10 in such manner as to firmly embrace the same, and a second body-part-circulation-permitting condition adapted to allow the free circulation of the body limb 10. The surface area and interface characteristics of the clamp members 14, 16 are selected to provide the intended first and second conditions thereof. To minimize the clamping pressure for a given tension, it is presently preferred that the interface of each clamp exhibit a maximum amount of friction between the clamp and the limb for a given clamping pressure. Any suitable mechanical, pneumatic or other clamping member, mechanism or device that may be caused to cyclically embrace so as to substantially immovably grip the body part and not to embrace so as to allow circulation to the flesh directly in contact therewith may be employed without departing from the inventive concept.

The link 18 preferably is rigid, and serves two primary functions. The one is to connect the first clamp 14 to the second clamp 16 so as to maintain them in intended orientation, and the second is to provide a connecting point for cable 19 which is attached to a means for generating tension 20. While in the illustrated embodiment two (2) clamps 14, 16 and a single rigid link 18 are preferred, it is envisaged that the link may have a different number of link members, and that a different number of clamps may be used.

A control unit 22 is relayed to both clamps 14 and 16 by control wires 24. The clamps 14, 16 are operated by the control unit 22 to coordinate the opening and closing of clamps 14 and 16 in an alternating fashion so that clamp 14 is caused to be constricted about the body part 10 while clamp 16 is caused to be loose enough to permit the flow of blood to the area which was directly in contact with clamp 16, and vice versa. After a predetermined period, such as fifteen minutes, the clamp 16 is then signaled to tighten. When clamp 16 is tight, clamp 14 is then signaled to loosen. This alternating cycle continues as long as desired to further the healing process. The body clamp 12 in this fashion thus allows a substantially constant tension to be applied to body part 10 without either penetrating the skin, tissues, and bone or cutting off the circulation thereto.

Figure 2:
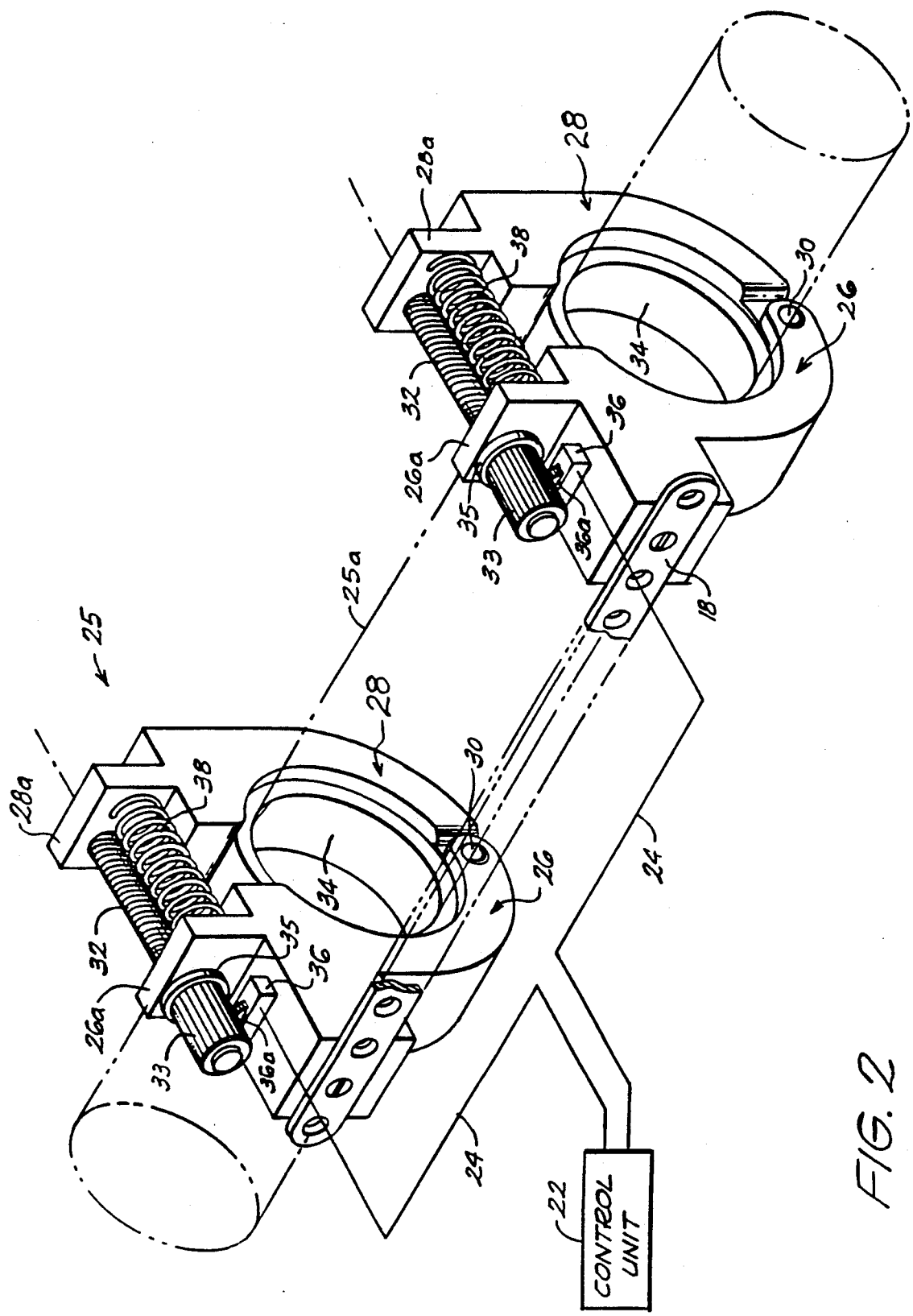
FIG. 2 is a perspective view of a presently preferred embodiment of the non-invasive body clamp of the invention.

Referring now to FIG. 2, which illustrates one presently preferred embodiment of the non-invasive body clamp of the invention, a clamp assembly generally designated 25 is shown about the body part schematically illustrated by phantom cylinder 25a and includes two movable arcuate cuffs generally designated 26 and 28, each cuff 26, 28 having an articulation 30 pivotally joining one pair of cuff ends, and each having a threaded bolt 32 joining the other ends. A foam insert 34 lines the interior of the cuffs 26, 28 to protect the skin along the surface of contact. The surface of the foam preferably exhibits a large coefficient of friction when in contact with both the cuff and the skin of the body part 25a. The cuff ends remote from the pivot 30 of each of the cuffs 26, 28 terminate in flanges 26a, and 28a respectively. The bolt 32 is fastened to flange 28a at one of its ends and is received through an opening provided therefor in flange 26a at the other of its ends for each of the cuffs 26, 28. A nut 33 is journaled at 35 to flange 26a of cuff 26 to the inside of which the corresponding bolt 32 is threadably engaged. A motor 36 drives gear 36a that is coupled to and rotatably drives nut 33 of each of the cuffs 26. In response to signals from control unit 22, the motors 36 and cooperative gears 36a cause the nuts 33 threaded to the bolts 32 of each of the cuffs 26, 28 to rotate relative to the corresponding flange 26a, the threads of which engage the threads of the bolts 32, thereby pushing apart or pulling together the opposing ends of the cuff ends of the corresponding cuffs 26 and 28 in dependance on the sense of rotation of the motors 36. A compression spring 38 mounted between flanges 26a, 28a is used to assist the cuffs 26, 28 to move to their open conditions.

Again, the control unit 22 is operative as described above in connection with the description of the FIG. 1 to so actuate the motors 36 that the cuffs are cyclically driven between their respective body-embracing and circulation allowing conditions and in such a way that one is always in its closed condition while the other is either being actuated to its open condition or already in its open condition. The mechanism of FIG. 2 is of course to be understood as solely exemplary, other embodiments being quite readily possible on the basis of the present invention. Further, changes are possible to the FIG. 2 mechanism, such as, to give one example, the replacement of the stationary bolt 32 with one that is journaled for rotation to the cuffs.

These and other examples of the concept of the invention illustrated above are intended by way of example and the actual scope of the invention is to be determined solely from the following claims.

What is claimed is:

1. Non-invasive apparatus for placing bones under tension, comprising:
   a first collar movable between an open and a closed condition;
   a second collar movable between an open and a closed condition;
   a rigid link connected between said first and second collars holding them in spaced-apart relation;
   means, coupled to said first and second collars, for cyclically moving the collars in such a way that while one is in the open condition and while being moved to the open and closed conditions the other remains in the closed condition; and
   a tensioning member attached to said rigid link.

2. The invention of claim 1, wherein said moving means includes a control unit.

3. The invention of claim 2, wherein said control unit is operative to interpose a delay that always maintains one collar in closed condition during transition of the other from the open to the closed condition.

4. The invention of claim 1, wherein said closed condition is sufficiently tight to remain slippage-free around an intended body part thereby to permit a constant tension to be applied to the body part by action of the tensioning member.

5. The invention of claim 4, wherein said cyclically moving means defines a cycle interval sufficient to allow blood to adequately circulate.

6. The invention of claim 1, wherein said first collar and said second collar each include a mechanically pivotable cuff assembly and each incorporate a motor coupled to a nut threaded to a bolt used to open and close said cuff.

7. The invention of claim 6, wherein said moving means includes a control unit.

8. The invention of claim 7, wherein said control unit ensures that each of said cuffs is in its closed condition prior to allowing the other of said cuffs to be in its open condition.

* * * * *